(12) United States Patent
Bhethanabotla et al.

(10) Patent No.: US 7,047,792 B1
(45) Date of Patent: May 23, 2006

(54) SURFACE ACOUSTIC WAVE HYDROGEN SENSOR

(75) Inventors: Venkat R. Bhethanabotla, Tampa, FL (US); Shekhar Bhansali, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/886,386

(22) Filed: Jul. 7, 2004

Related U.S. Application Data

(60) Provisional application No. 60/481,063, filed on Jul. 7, 2003.

(51) Int. Cl.
*G01N 29/00* (2006.01)

(52) U.S. Cl. ..................... 73/24.01; 73/24.06

(58) Field of Classification Search ............. 73/24.01, 73/24.06
See application file for complete search history.

(56) References Cited

U.S. PATENT DOCUMENTS 5,045,285 A * 9/1991 Kolesar, Jr. ................. 422/98
6,029,500 A 2/2000 Tom ......................... 73/31.05

OTHER PUBLICATIONS

Favier, Frederic et al., Hyrdrogen Sensors and Switches from Electrodeposited Palladium Mesowire Arrays, Science, Sep. 21, 2001, pp. 2227-2231, vol. 293.

Jakubik, Wieslaw et al., Bilayer Structure for Hydrogen Detection in a Surface Acoustic Wave Sensor System, Sensors and Actuators, 2002, pp. 265-271, B-82.

* cited by examiner

*Primary Examiner*—Daniel S. Larkin
(74) *Attorney, Agent, or Firm*—Smith & Hopen, P.A.; Molly Sauter

(57) ABSTRACT

The present invention provides a delay line SAW device fabricated on a lithium niobate substrate and coated with a bilayer of nanocrystalline or other nanomaterials such as nanoparticles or nanowires of palladiumn and metal free pthalocyanine which will respond to hydrogen gas in near real time, at low (room) temperature, without being affected by CO, $O_2$, $CH_4$ and other gases, in air ambient or controlled ambient, providing sensitivity to low ppm levels.

23 Claims, 13 Drawing Sheets

FIG. 4

| Parameter | Value |
|---|---|
| Piezoelectric Crystal | Y-Z Lithium Niobate |
| Surface Acoustic Wave Velocity ($v_0$) | 3488 m/s |
| Center Frequency ($f_0$) | 200 MHz |
| Design Impedance (Z) | 50 ohm |
| No. of Finger Pairs ($N_p$) on a single IDT | 50 |
| Delay Path Length (L) (in terms of wavelength $\lambda$) | 300$\lambda$ |
| Capacitance/finger pair-length ($C_0$) | 4.6 pF/cm |
| Normalized surface particle velocity in x-direction ($\frac{v_{x0}^2}{\omega P}$) | 0 cm.g |
| Normalized surface particle velocity in y-direction ($\frac{v_{y0}^2}{\omega P}$) | 0.83 x $10^{-6}$ cm.g |
| Normalized surface particle velocity in z-direction ($\frac{v_{z0}^2}{\omega P}$) | 0.56 x $10^{-6}$ cm.g |
| Electromechanical coupling coefficient (squared) ($K^2$) | 4.8 % |

FIG. 5
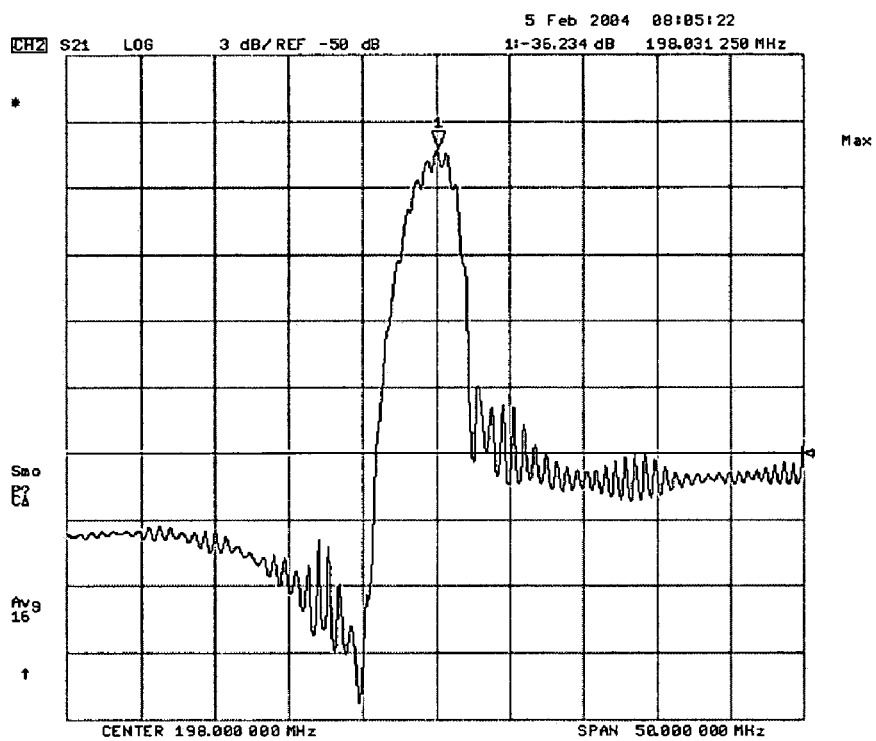
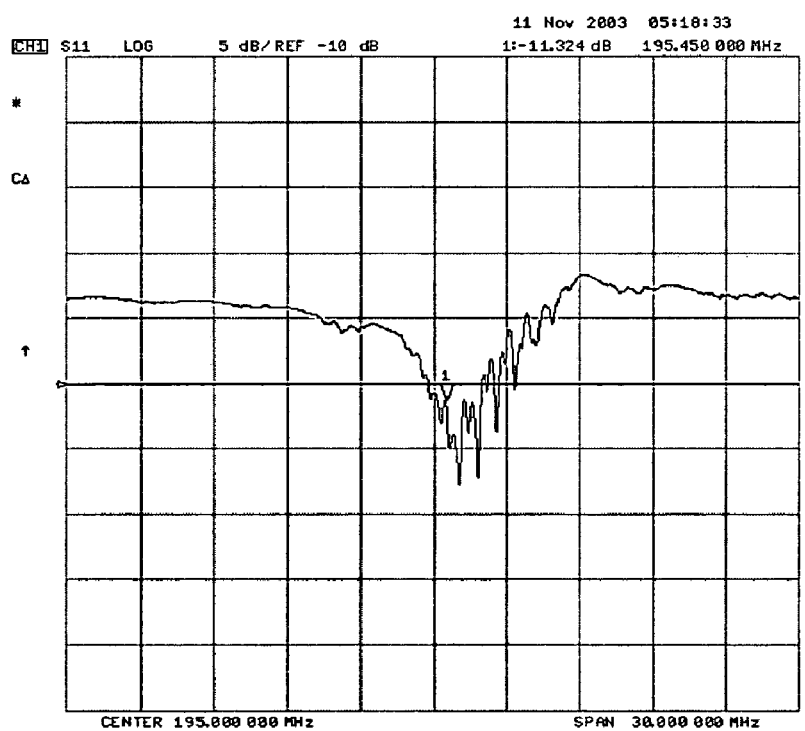

FIG. 8

| % H$_2$ | 2% | 63% | 99% |
|---|---|---|---|
| 0.50% | 27 | 707 | 1257 |
| 1% | 20 | 850 | 2200 |
| 2% | 27 | 61 | 111 |
| 3% | 26 | 131 | 231 |
| 4% | 14 | 85 | 179 |
| 5% | 7 | 75 | 172 |
| 6% | 10 | 79 | 99 |

FIG. 9

| Percent Hydrogen | Frequency Change |
|---|---|
| 4.0 | 45 kHz |
| 2.0 | 43 kHz |
| 1.0 | 30 kHz |
| 0.5 | 20 kHz |

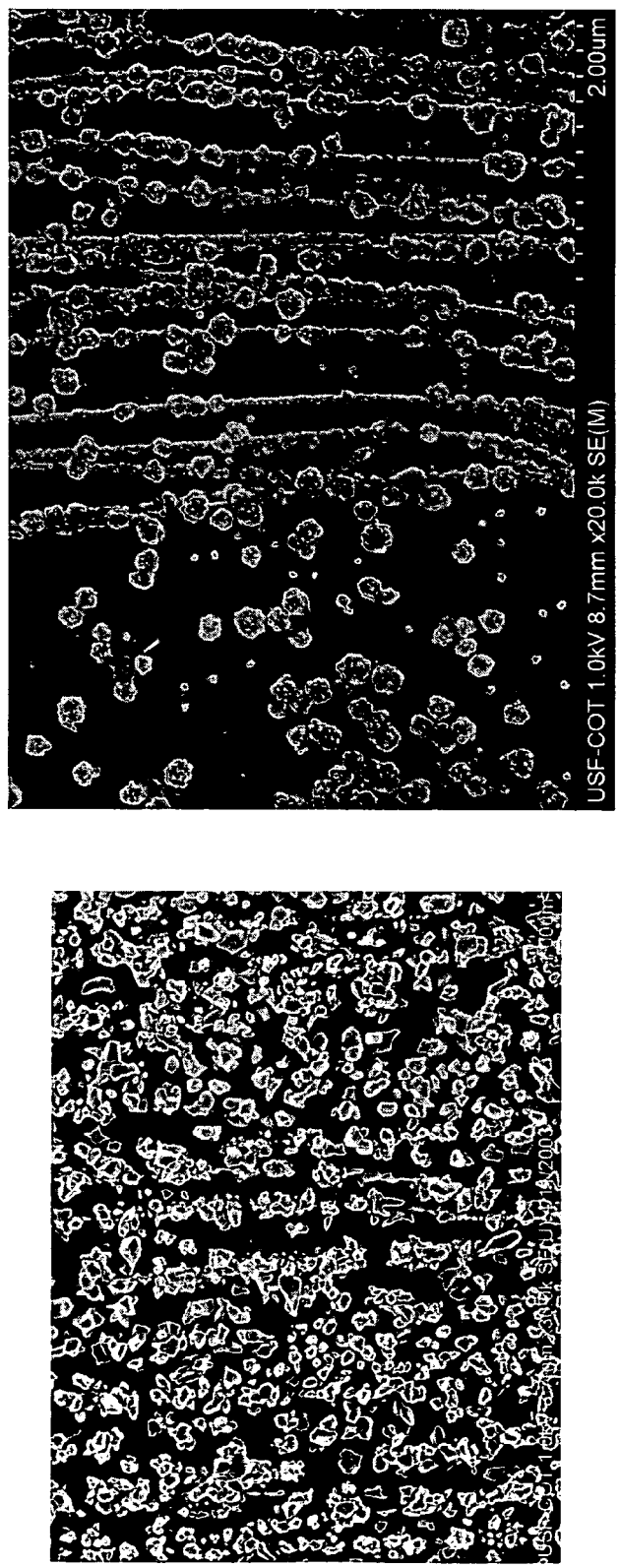
Fig. 12 Electrodeposited Palladium Nanoparticles and Wires on Graphite Step Edges (~60 nm)

Fig. 13 Synthesized Anodic Alumina Templates (40 nm, ordered pores)
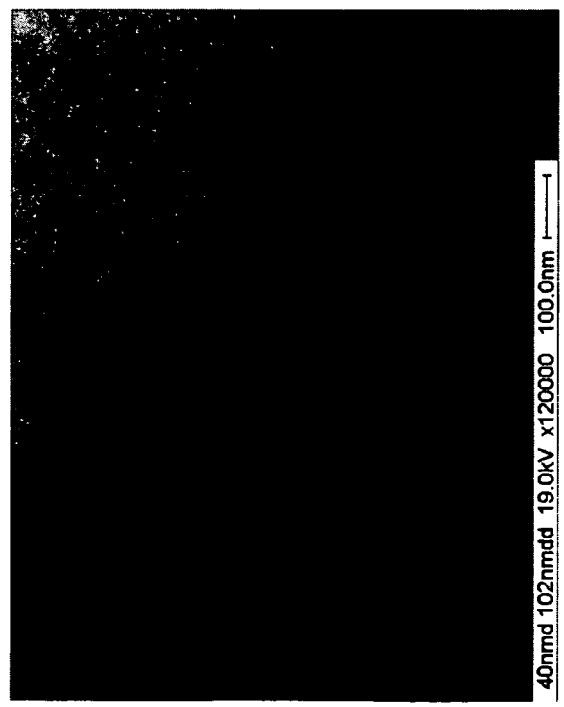

SURFACE ACOUSTIC WAVE HYDROGEN SENSOR

CROSS REFERENCE TO RELATED APPLICATIONS

This application claims priority to U.S. Provisional Patent Application No. 60/481,063, entitled, "Nano-Wire and Nano-Particle Based SAW and QCM Sensor", filed Jul. 7, 2003.

STATEMENT OF GOVERNMENT INTEREST

This invention was made with Government support under Grant No. 2106353 awarded by NASA/FSEC. The Government has certain rights in the invention.

BACKGROUND OF INVENTION

Hydrogen gas is used in the process of manufacturing semiconductors, and has gained popularity as a clean source of energy or as a fuel gas. However, the increasing use of hydrogen gas should not be considered as one without disadvantages. In fact, a number of problems arise involving the storage of this gas. A hydrogen leak in large quantities should be avoided because hydrogen, when mixed with air in the ratio of approximately 4.65:93.9 volume % is explosive. Hence, it is important to develop highly sensitive hydrogen detectors to prevent accidents due to its leakage, thus, saving lives and infrastructure. Such detectors should allow continuous monitoring of the concentration of the gas in the environment in a quantitative and selective way.

Hydrogen sensors employing various techniques are known in the art. Palladium gated MOS devices have been used employing a variety of semiconducting materials. These devices suffer from high operating temperatures, high power requirements and slow response times. Doped metal oxides, typically $SnO_2$, for use as hydrogen sensors are known in the art. While these devices are capable of low level detection, they suffer from high power consumption, slow response times, and are not thermally stable at the high operating temperatures required. Palladium nanowire arrays exhibiting increasing conductivity upon exposure to hydrogen have been used as sensors. The palladium nanowire array devices exhibit fast response times, low power consumption, and room temperature operation. However, the palladium nanowire array devices available to date require a predetermined nanowire array structure and do not exhibit the desired low level detection for a hydrogen sensor.

Among the hydrogen sensors employing palladium, piezoelectric sensors are have also been described in the literature, and are not currently used commercially. These sensors are based on piezoelectric crystals, which allow transduction between electrical and acoustic energies. There are mainly two hydrogen sensors in this category: quartz crystal microbalance (QCM) and surface acoustic wave sensors (SAW). The response in these sensors arises due to the change in wave properties upon adsorption of hydrogen on a palladium surface.

Surface acoustic wave sensors fall under the category of mass sensors and use changes in the acoustic wave transmission through a substance to detect changes in mass loading. It has been shown that chemical vapor sensing can be accomplished using a device originally designed as a delay-line. Currently available surface acoustic wave (SAW) sensors utilize frequencies on the order of 100 MHz. The most commercially developed of the acoustic wave sensors is the thickness shear mode (TSM) device, also known as the quartz crystal microbalance (QCM).

One of the advantages of SAW sensors is their ability to accommodate very high sensitivities without resorting to pre-concentration. This allows for considerations of sensors relevant to environmental monitoring also, in addition to detection for leaks and health related applications. While ppb levels of detection are indeed possible with SAW devices, most applications of this sensor so far have been for organics using polymer sensing layers with higher levels of gas phase concentrations.

Since the surface wave or acoustic velocity is much slower than the speed of light, an acoustic wavelength is much smaller than its electromagnetic counterpart. This results in the SAW's unique ability to incorporate an incredible amount of signal processing or delay in a very small volume. As a result of this relationship, physical limitations exist at higher frequencies when the electrodes become too narrow to fabricate with standard photolithographic techniques and at lower frequencies when the devices become impractically large.

SAW devices are favored for use in chemical sensing applications because of their small size, low cost, high sensitivity and reliability. Most SAW chemical sensors monitor changes of the SAW phase velocity and attenuation as the vapor interacts with the sensing layer. The shift in the phase velocity and/or attenuation is measured by recording the frequency and insertion loss of the SAW device, respectively. Various effects, including mass loading, viscoelastic loading, and acousto-electric coupling, contribute to SAW sensor response. Typical chemical sensors take advantage of one or more of these mechanisms.

While it is known in the art to use SAW devices with a palladium sensing layer to detect hydrogen gas, an improved sensor is needed in the art that provides near real-time monitoring. An improved hydrogen sensor needs to be operable within a wide temperature range and be sensitive to very low levels of hydrogen. Additionally, the sensor should exhibit a small response time, low power consumption and be resistant to the fouling effects of other gases present, including CO, $O_2$, $CH_4$ and other gases.

However, in view of the prior art considered as a whole at the time the present invention was made, it was not obvious to those of ordinary skill in the pertinent art how the identified need could be fulfilled.

SUMMARY OF THE INVENTION

The longstanding but heretofore unfulfilled need for a hydrogen sensor that exhibits desired characteristics superior to hydrogen sensors known in the art is now met by a new, useful, and non-obvious invention.

In accordance with the present invention is provided a hydrogen gas sensor including a surface acoustic wave device fabricated on a lithium niobate substrate and a sensing bilayer positioned on the acoustic path of the surface acoustic wave device, the sensing bilayer further comprising nanocrystalline or other nanomaterial such as nanoparticles or nanowires of palladium and metal free phthalocyanine.

In a preferred embodiment, the surface acoustic wave device has a center frequency of about 200 MHz. However, surface acoustic wave devices designed and fabricated to have a different center frequency are within the scope of the present invention.

Additionally, in another embodiment, the thickness of the metal free phthalocyanine layer of the sensing bilayer is about 100 nm. This is not meant to be limiting and other layer thicknesses are within the scope of the present invention.

The sensing bilayer in accordance with the present invention comprising two or more layers that takes advantage of the mass, modulus and/or electro-acoustic perturbation mechanisms of the SAW sensor The sensing bilayer in accordance with the present invention may additionally comprise a nanocrystalline or other nanomaterial such as nanoparticles or nanowires of metal and/or alloy selected from nickel, palladium, platinum or silver, with palladium being a most preferred single metal species. The foregoing metal species may be utilized in combination with one another in the form of alloys or blends of two or more of such metals, or a metal of such type may be used in combination in an alloy blend or composite, with other materials. As an example, a Pd/Ni alloy would be effective in the present invention and also provide mechanical stability against the expansion caused by hydrogen absorption.

The surface acoustic wave device in accordance with the present invention may be selected from a group of SAW device commonly employing a delay line. Additionally, the SAW device may be a dual delay line surface acoustic wave device.

In employment of the device as a hydrogen sensor, the surface acoustic wave device and accompanying sensing layer is positioned with an environment. An input voltage applied to the surface acoustic wave device results in the surface acoustic wave device exhibiting a frequency response. Accordingly, the sensing bilayer interacts and reversibly changes the frequency response of the surface acoustic device upon exposure to hydrogen gas in the environment and a sensor output is provided for outputting the change in the frequency response of the surface acoustic device. As a result, the sensor is effective in the detection of hydrogen gas at a concentration of from 0% to at least 30%. Preferably, the hydrogen sensor is sensitive to hydrogen at a concentration of 0.05%. The hydrogen gas sensor in accordance with the present invention is sensitive to hydrogen in air and in inert atmospheres.

With the use of high frequency SAWs, novel sensing layers such as those described in accordance with the present invention, the use of sensing layers comprising two or more layers that take advantage of the mass, modulus and/or electro-acoustic perturbation mechanisms of the SAW sensor, the present invention provides SAW sensing technologies for environmental gas monitoring at the required low ppb levels. Using higher frequencies devices fabricated using modern fabrication techniques are also within the scope of the present invention.

Acoustic wave sensors are economical, rugged, sensitive and reliable. Capability of being passively and wirelessly interrogated is additionally within the scope of the invention, with such devices having the potential for use in distributed sensing applications.

BRIEF DESCRIPTION OF DRAWINGS

For a fuller understanding of the nature and objects of the invention, reference should be made to the following detailed description, taken in connection with the accompanying drawings, in which:

FIG. 4 presents a table of the independent parameters of the SAW device presented in the exemplary embodiment;

FIG. 5 illustrates the S parameter results for the 200 MHz device in accordance with the exemplary embodiment;

FIG. 8 illustrates the response times, in seconds, of the exemplary sensor at different concentrations of hydrogen. These times include the transportation lag of the gas in the gas lines to the sensor, on the order of 8 to 30 seconds. Hence, the actual response time of the sensor is much smaller than shown in the table of this FIG. 8;

FIG. 9 illustrates the average frequency shifts at different hydrogen percentages for the exemplary sensor;

FIG. 12 is an SEM electrodeposited palladium nanoparticles and wires on graphite step edges; and FIG. 13 is an SEM of synthesized anodic alumina templates.

DETAILED DESCRIPTION OF PREFERRED EMBODIMENT

The present invention is based on the finding that Pd and Pd alloys reversibly interact with hydrogen and can be used in combination with a surface acoustic wave device exhibiting a piezoelectric effect to provide an effective sensor for hydrogen gas in air and inert environments.

It is known that acoustic waves can be generated in piezoelectric materials. The piezoelectric material may be either a polished substrate such as quartz, lithium niobate, lithium tantalate or a thin film such as zinc oxide. Quartz is the most commonly used substrate because of its temperature stability for certain crystal orientations. However, for high acousto-electric coupling applications, lithium niobate is preferred over quartz. Thin films of zinc oxide deposited on a non-piezoelectric substrate such as silicon are used when the device needs to be integrated with microelectronics. The crystal orientation, the thickness of the piezoelectric material and the geometry of the metal transducers determine the type and mode of the acoustic waves.

Figure 1:
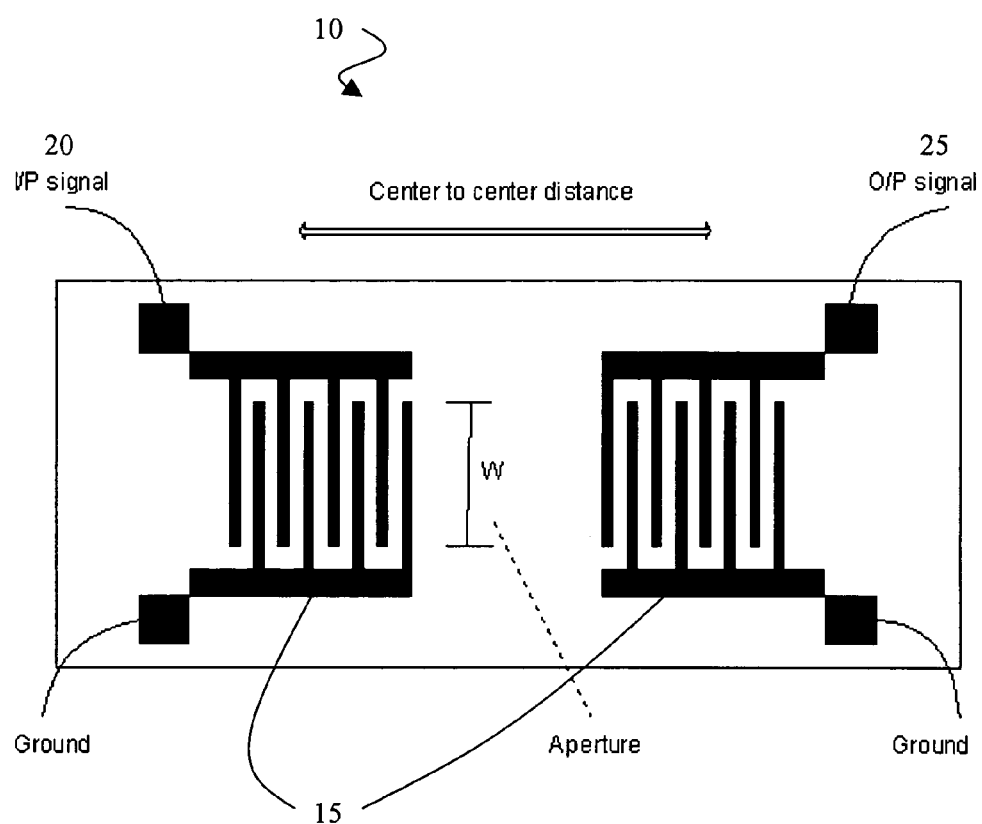
FIG. 1 Prior art schematic of SAW delay line.

In a delay-line SAW device 10, surface acoustic waves are generated using interdigital metal transducers 15 (IDT) patterned on a substrate as shown with reference to FIG. 1. One set of the IDT 15 is used as a transmitter that converts the applied voltage variation 20 into acoustic waves and the other IDT 15 receives these acoustic waves and converts them back to an output voltage 25. Amplitude of particle displacement is on the order of a wavelength.

Figure 2:
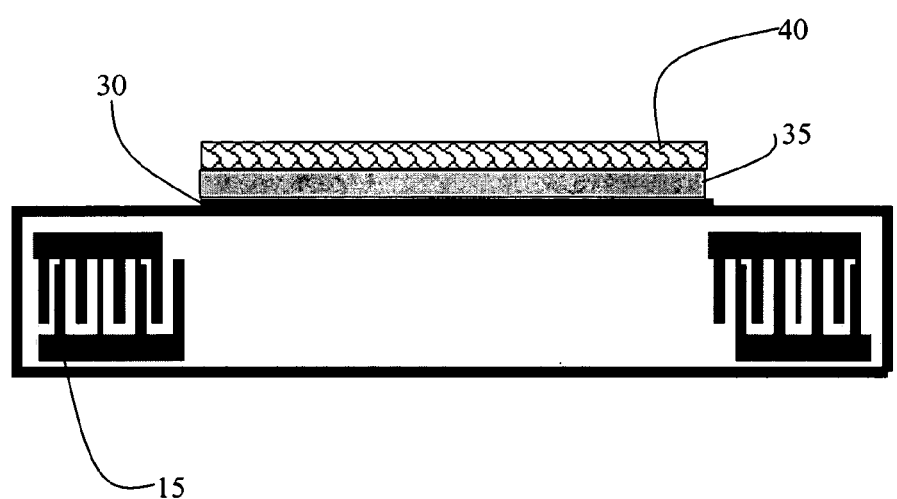
FIG. 2 Exemplary illustration of hydrogen sensor elements in accordance with the present invention.

In an exemplary embodiment, with reference to FIG. 2, the hydrogen sensor of the present invention includes a SAW device with dual delay lines as previously described. In this embodiment, the delay lines 15 are fabricated on to a lithium niobate substrate 30. The sensing bilayer, including nanocrystalline palladium 35 is fabricated onto a thin layer of metal free phthalocyanine 40. The layers described may be fabricated using electrodeposition, sputtering and electron beam evaporation techniques known in the art, after suitable optimization, which is an important part of the art demonstrated in this invention. FIGS. 12 and 13 illustrate nanomaterial palladium deposition techniques in accordance with the present invention. FIG. 12 is an illustration of SEM electrodeposited palladium nanoparticles and wires on graphite step edges, and FIG. 13 is an SEM of synthesized anodic alumina templates of nanoparticle palladium.

The measured response of the surface acoustic wave device arises from the perturbations in wave propagation characteristics, specifically wave velocity & attenuation, resulting from interactions between the surface acoustic wave and the surface layer. As SAWs propagating in a piezoelectric medium generate both mechanical deformation and an electrical potential, there are both mechanical and electrical couplings between SAW device and the sensing bilayer.

In accordance with the present invention, lithium niobate was selected as the optimum substrate due to its high acousto-electric effect in sensor response. Low frequency SAW devices of up to 200 MHz have been fabricated on lithium niobate using traditional optical lithography. Additionally, high frequency devices, 900 MHz, have been fabricated using electron beam lithography due to the submicron line widths of the IDTs required.

After the fabrication of the SAW delay line by the above procedures, the sensing layer is deposited on the acoustic path of the SAW device. The sensing layer consists of a bilayer of metal free phthalocyanine and nanocrystalline or other nanomaterial such as nanoparticles or nanowires of palladium.

In a particular embodiment, the sensing layer is deposited using a shadow mask made up of aluminum which protects the IDTs. The wafer and mask are then aligned so that the acoustic path of delay line is exposed. A thin layer of metal free phthalocyanine is then coated by using sublimation. The process is carried out in a chamber under a vacuum of around 5×10-5 Torr. In one embodiment, the powdered metal free phthalocyanine may be contained in a baffled tantalum box covered with sieved lid. This specialized box is required to direct the vapors straight and to get material deposited on the target wafer which is mounted at a large distance from the source. The thickness of the phthalocyanine layer is between 100 nm and 115 nm.

Figure 3:
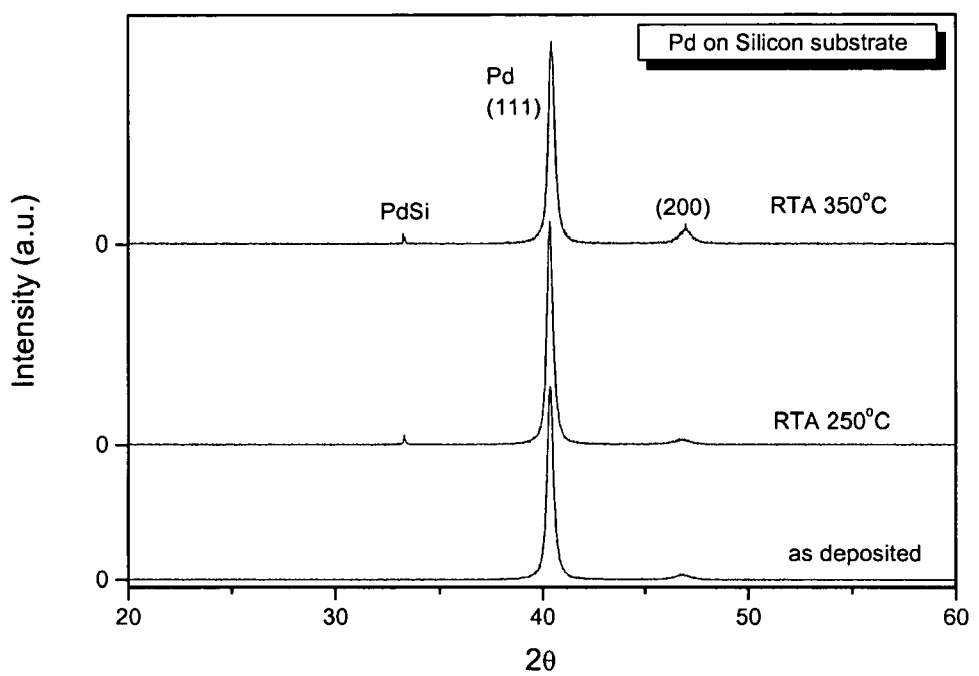
FIG. 3 XRD plot of the nano-crystalline Pd film in accordance with the present invention.

Nanocrystalline thin films are known to have much larger grain boundary volume in the material, leading to increased rates of diffusion of gases. Nanocrystalline thin films of several materials such as Cu, Fe, Mo and Si have been deposited using sputtering. FIG. 3 illustrates an XRD plot of the nano-crystalline Pd film in accordance with the present invention. In a particular embodiment, fabrication of Pd films is carried out by sputtering using a multi-gun sputterer at pressures of $1.7 \times 10^{-2}$ Torr to $5 \times 10^{-2}$ Torr. These films are subjected to rapid thermal annealing at 250 and 350° C. X ray diffraction (XRD) measurements on these films revealed that Pd crystallizes as deposited. XRD profiles are shown in FIG. 3. For deposited films, these showed reflections of (111) and (200) peaks, both broadened, indicating nanocrystalline nature of the films. From these profiles, a crystallite size of approximately 30 nm was obtained.

The sensing bilayer reversibly interacts with hydrogen gas resulting in a mass change and electro-acoustic effects. As a result, the frequency response characteristics of the SAW device are altered from the original frequency characteristics prior to contact with the gas. Such frequency changes are then used to generate a suitable output indicating the presence of hydrogen. A source of electrical excitation is used to provide an oscillating electrical field to the SAW device. Additional electronics are used to sample the output resonant frequency of the SAW when the oscillating field is applied to determine the change in resonant frequency from the fundamental frequency when the sensing bilayer interacts with hydrogen being monitored, thereby generating an output indicative of the presence of hydrogen in the environment. The high acoustic-electric coupling provided by the lithium niobate substrate, the low sensitivity and quick response time of the nanocrystallline or other nanomaterial such as nanoparticles or nanowires of palladium and the thin layer of metal free phthalocyanine provide a hydrogen sensor having improved characteristics over other devices known in the art.

The features and advantages of the invention are more fully illustrated by the following non-limiting example.

EXAMPLE

The table of FIG. 4 provides the independent parameters for the SAW device of this exemplary embodiment.

The complete characterization of an acoustic wave device is always obtained from a complete frequency response spectrum including all the scattering parameters. Scattering parameters (S-parameters) are the set of parameters describing the scattering and reflection of traveling waves when a network is inserted into a transmission line. S-parameters are normally used to characterize high frequency networks, where simple models valid at lower frequencies cannot be applied. S-parameters are normally measured as a function of frequency.

For each port, the incident (applied) and reflected wave properties are measured. When the incident wave travels through the network, its value is multiplied (i.e. its gain and phase are changed) by scattering, thus giving the resulting output value. S-parameters can be considered as the gain of the network, and the subscripts denote the port numbers. The ratio of the output of port 2 to the incident wave on port 1 is designated $S_{21}$. Likewise, for reflected waves, the signal comes in and out of the same port, hence the S-parameter for the input reflection is designated $S_{11}$. For a two port network, (assuming use of matched loads and characteristic impedance of 50 ohms), $S_{11}$ is the reflection coefficient of the input, $S_{22}$ is the reflection coefficient of the output, $S_{21}$ is the forward transmission gain, and $S_{12}$ is the reverse transmission gain From output to input, S parameters are used to help characterizing a network. They have a specific importance for high frequency applications. S parameters as seen above are voltage ratio, so they have no units. In practical usage, S parameters are expressed in dB.

S parameters are complex values, with magnitude and phase, and are measured using a Vector Network Analyzer, VNA, which is capable of measuring both the magnitude and the phase of a signal simultaneously. The S parameter results for the 200 MHz device in accordance with the present example are shown with reference to FIG. 5.

Figure 6:
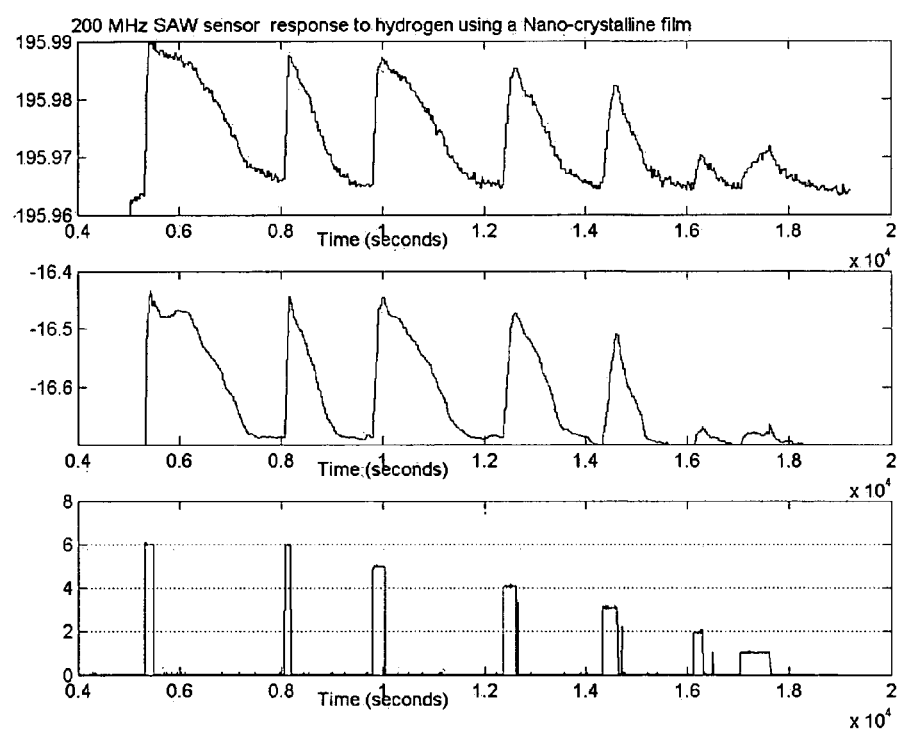
FIG. 6 illustrates the response of the 200 MHz SAW sensor coated with 115 nm metal free phthalocyanine and 200 nm nano-crystalline films for a first run.
Figure 7:
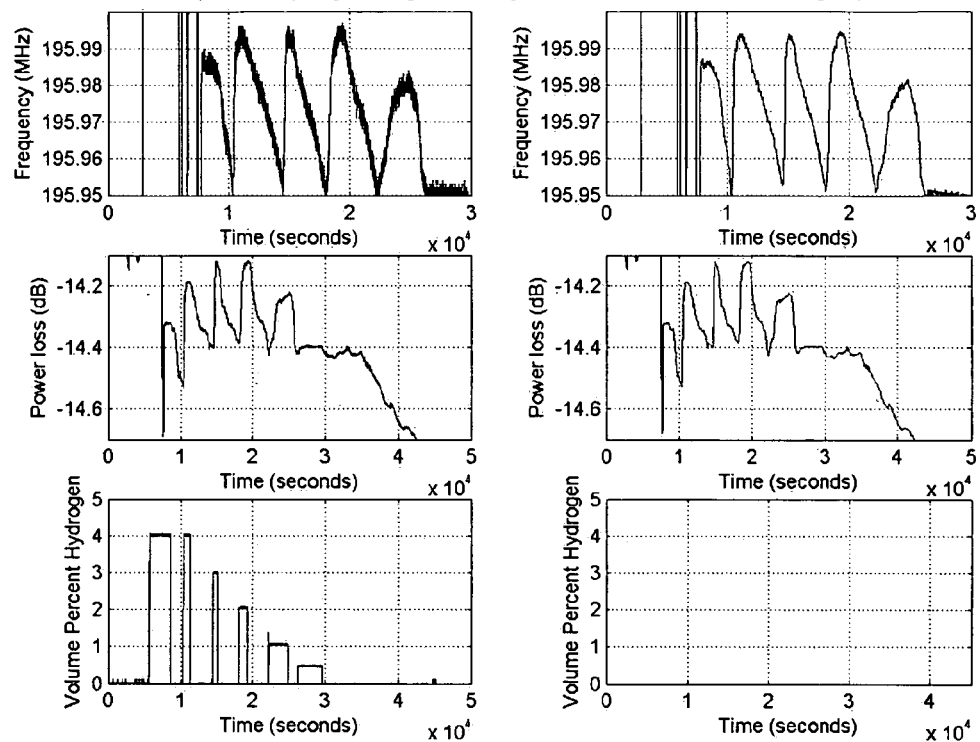
FIG. 7 illustrates the response of the 200 MHz SAW sensor coated with 115 nm metal free phthalocyanine and 200 nm nano-crystalline films for a second run.

The responses of the 200 MHz SAW sensor coated with 115 nm metal free phthalocyanine and 200 nm nano-crystalline films for two different runs are shown in FIG. 6 and FIG. 7. The tests were carried out at room temperature inside the test cell. The hydrogen was cycled when the maximum center frequency of the device repeated its value for a couple of minutes. As shown in the figures, different concentrations of hydrogen ranging from 1% to 6% were tried. Desired concentration of hydrogen was achieved by mixing it with nitrogen. The flow rate was kept at a total of 1000 SCCM.

The response times of this sensor at different concentrations of hydrogen are shown in FIG. 8. This time includes the time it takes for the hydrogen to reach the test cell. The transport lag was calculated, and it is roughly 8–30 seconds, depending on the concentration.

FIG. 9 illustrates the average frequency shifts at different hydrogen percentages for the exemplary sensor.

Figure 10:
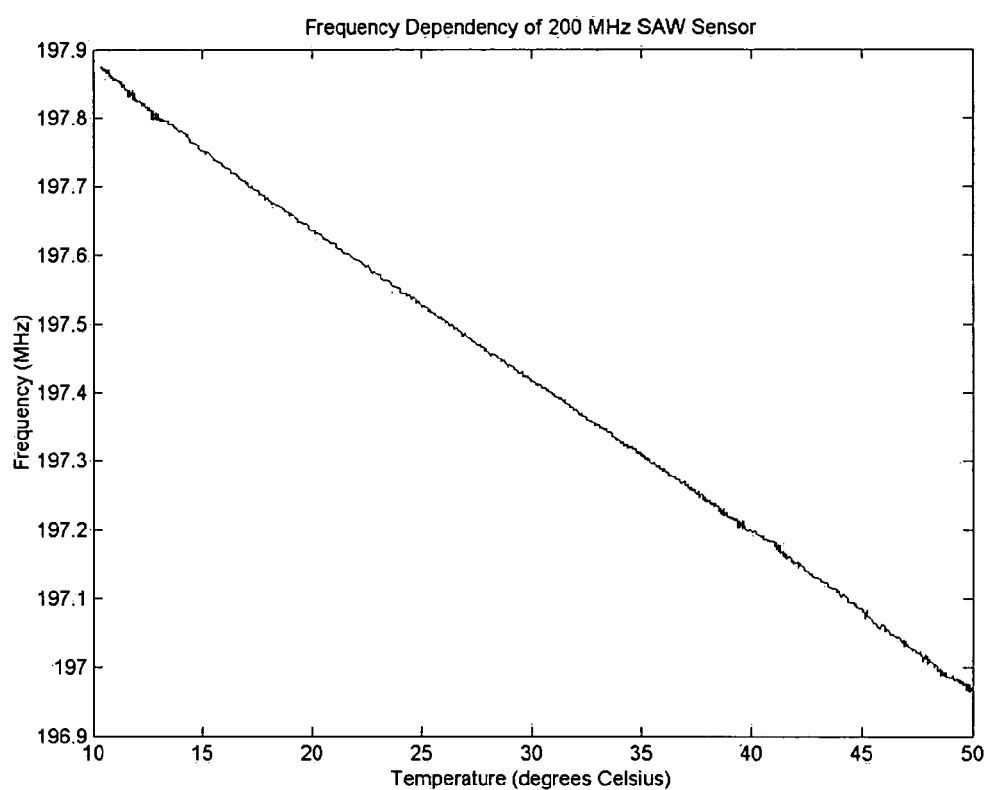
FIG. 10 illustrates the effect of a change in temperature on the acoustic wave device performance of the exemplary embodiment.

The graph of FIG. 10 illustrates the effect of a change in temperature on the acoustic wave device performance. Changes in temperature produce change in the density of the substrate material which in turn changes the velocity of acoustic wave. There are three main methods by which the effects of temperatures can be minimized: use of low temperature coefficient material such as Quartz, incorporation of a temperature sensor and compensation circuitry or in-situ control of the temperature. The stringent need for temperature control can be taken care of by using a dual delay line SAW device. In dual delay line configuration, one delay line is coated with the sensing layer while other is left uncoated. Measuring the difference between the two device parameters, all the external effects including temperature will be mostly nullified, except for the very local effects from the heats of adsorption and absorption. One more advantage of this particular set up is that the resultant frequency shifts due to the analyte absorption will be in KHz range and can be measured very easily and economically.

Figure 11:
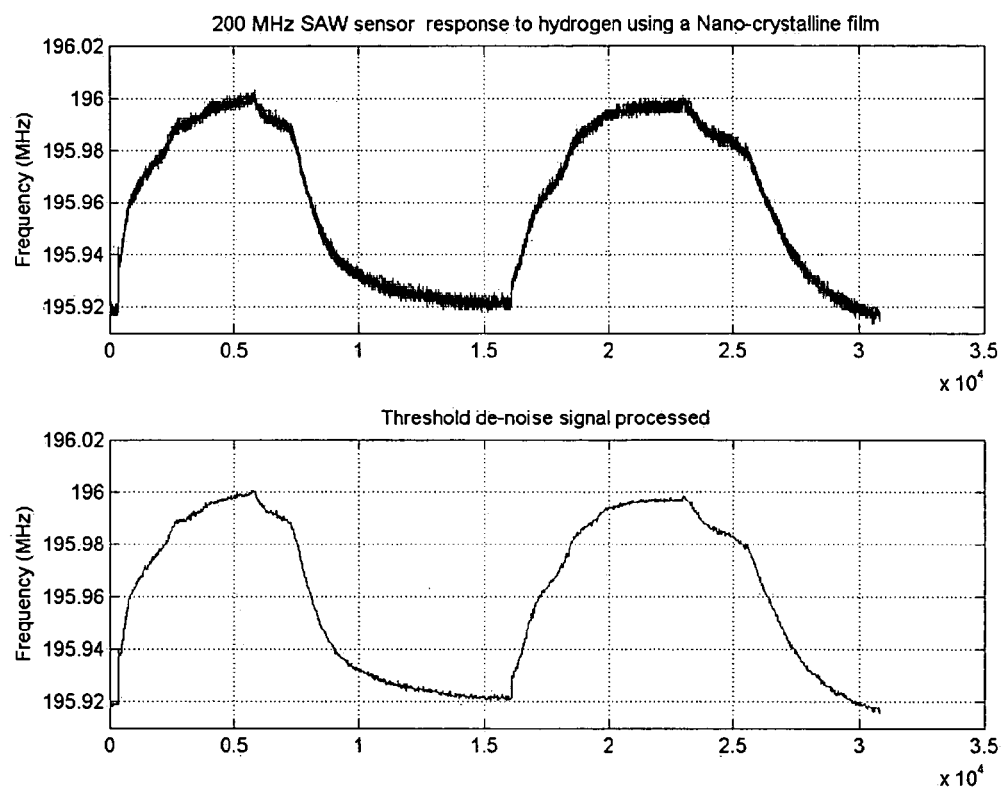
FIG. 11 illustrates the results of a repeatability study for the sensor of the exemplary embodiment.

The repeatability of the sensor was studied, and the results present in reference to FIG. 11. In this study, a pulse of 1% hydrogen was cycled at room temperature. As shown in FIG. 11, the sensor shows very good repeatability with a frequency shift of around 40 KHz every time when there are no temperature fluctuations. The second peak is widened because hydrogen pulse duration was longer than the previous one.

As shown by this exemplary embodiment, an hydrogen sensor is provided having improved characteristics over other sensors known in the art. The present invention provides a delay line SAW device, coated with a bilayer of nanocrystalling Pd and metal free pthalocyanine which will respond to hydrogen gas in near real time, at low (room) temperature, without being affected by CO, $O_2$, $CH_4$ and other gases, in air ambient or controlled ambient, providing sensitivity to low ppm levels.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A hydrogen gas sensor, comprising: a surface acoustic wave device fabricated on a lithium niobate substrate; and a sensing bilayer positioned on the acoustic path of the surface acoustic wave device, the sensing bilayer further comprising nanomaterial palladium and metal free phthalocyanine.

2. The hydrogen gas sensor of claim 1, wherein the nanomaterial palladium is nanocrystalline palladium.

3. The hydrogen gas sensor of claim 1, wherein the nanomaterial palladium is nanoparticle palladium.

4. The hydrogen gas sensor of claim 1, wherein the nanomaterial palladium is nanowire palladium.

5. The hydrogen gas sensor of claim 1, wherein the surface acoustic wave device has a center frequency of about 200 MHz.

6. The hydrogen gas sensor of claim 1, wherein the nanomaterial palladium further comprises an alloy of palladium and nickel.

7. The hydrogen gas sensor of claim 1, wherein the nanomaterial palladium further comprises an alloy of palladium and silver.

8. The hydrogen gas sensor of claim 1, wherein the nanomaterial palladium further comprises an alloy of palladium and platinum.

9. The hydrogen gas sensor of claim 1, wherein the nanomaterial palladium further comprises nanomaterial palladium dispersed in a polymer film.

10. The hydrogen gas sensor of claim 1, wherein the thickness of the phthalocyanine layer is about 100 nm.

11. The hydrogen gas sensor of claim 1, wherein the surface acoustic wave device is a delay line surface acoustic wave device.

12. The hydrogen gas sensor of claim 1, wherein the surface acoustic wave device further comprises a dual delay line surface acoustic wave device.

13. The hydrogen gas sensor of claim 1, wherein the surface acoustic wave device has a center frequency of 200 MHz.

14. The hydrogen gas sensor of claim 1, further comprising: an input voltage applied to the surface acoustic wave device, the surface acoustic wave device exhibiting a frequency response; the sensing bilayer reversibly changing the frequency response of the surface acoustic device upon exposure to hydrogen gas; and a sensor output for outputting the change in the frequency response of the surface acoustic device.

15. The hydrogen gas sensor of claim 1, which is sensitive to hydrogen at a concentration of from 0% to 100%.

16. The hydrogen gas sensor of claim 15, wherein the sensing bilayer comprises metal free phthalocyanine and one or more nanomaterial metal species selected from the group consisting of nickel, palladium, platinum, and silver.

17. The hydrogen gas sensor of claim 15, wherein the sensing bilayer comprises a metal species selected from the group consisting of palladium, platinum, nickel, silver, alloys of two or more of the aforementioned metals, and alloys containing one or more of the aforementioned metals with other metal species.

18. The hydrogen gas sensor of claim 1, which is sensitive to hydrogen at a concentration of 0.05%.

19. The hydrogen gas sensor of claim 1, which is sensitive to hydrogen in air and in inert atmospheres.

20. A hydrogen gas sensor, comprising: a surface acoustic wave device fabricated on a lithium niobate substrate; and a sensing bilayer positioned on the acoustic path of the surface acoustic wave device, the sensing bilayer further comprising a nanomaterial palladium and metal free phthalocyanine.

21. The hydrogen gas sensor of claim 20, wherein the nanomaterial palladium is nanocrystalline palladium.

22. The hydrogen gas sensor of claim 20, wherein the nanomaterial palladium is nanoparticle palladium.

23. The hydrogen gas sensor of claim 20, wherein the nanomaterial palladium is nanowire palladium.

* * * * *